(12) United States Patent
Sekino et al.

(10) Patent No.: US 6,740,267 B1
(45) Date of Patent: May 25, 2004

(54) METHOD OF PRODUCING CERAMIC CROWNS

(75) Inventors: Masato Sekino, Tokuyama (JP);
Masaaki Ushioda, Tokuyama (JP);
Kyoichi Fujinami, Tokuyama (JP);
Osamu Iwamoto, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 320 days.

(21) Appl. No.: 09/831,709
(22) PCT Filed: Sep. 13, 2000
(86) PCT No.: PCT/JP00/06288
§ 371 (c)(1), (2), (4) Date: May 14, 2001
(87) PCT Pub. No.: WO01/21088
PCT Pub. Date: Mar. 29, 2001

(30) Foreign Application Priority Data

Sep. 20, 1999 (JP) ............................................. 11-265868

(51) Int. Cl.[7] .............................................. A61C 13/08
(52) U.S. Cl. ............................................ 264/19; 264/20
(58) Field of Search ................................ 264/16, 19, 20

(56) References Cited

U.S. PATENT DOCUMENTS 3,058,216 A * 10/1962 Cohen
4,265,669 A * 5/1981 Starling et al.
5,948,129 A * 9/1999 Nonami et al.

* cited by examiner

*Primary Examiner*—Christopher A. Fiorilla
(74) *Attorney, Agent, or Firm*—Sherman & Shalloway

(57) ABSTRACT

A method of preparing a ceramic artificial crown by applying at least one kind of dental porcelain onto the surface of a ceramic core molded by heating and softening a ceramic material and putting it into a mold with the application of a pressure followed by firing; wherein said mold is the one formed by burning a wax pattern after having removed a crucible former from an assembly which makes it possible to efficiently prepare a fully ceramic artificial crown of a high quality in a short period of time.

22 Claims, 3 Drawing Sheets

METHOD OF PRODUCING CERAMIC CROWNS

This application is a 371 of PCT/JP00/06288 filed Sep. 13, 2000.

TECHNICAL FIELD

The present invention relates to a method of preparing a fully ceramic artificial crown and a preparation kit used therefor.

BACKGROUND ART

In an aesthetic crown or inlay restration, a material obtained by baking a pottery material called metal-bonded porcelain onto a metal core has heretofore been used. However, this dental prosthetic material has a problem in that the gum undergoes the discoloration due to elution of metal ions. Another problem is that a metal in the core shuts off light making it difficult to reproduce transparent feeling as that of a natural tooth.

On the other hand, a fully ceramic artificial crown (also called all ceramic artificial crown) of which the core, too, is formed of ceramics does not cause the gum to be discolored by the elution of metal ions, since no metal core is used. Besides, since a material having a transparent feeling close to a natural tooth is used as the ceramic core, it is made possible to realize a natural transparent feeling and to obtain a color feeling closer to a natural tooth due to the lamination of a special porcelain. So far, a metal has in many cases been used as a core of the artificial crown from the standpoint of strength. In recent years, however, technology has been developed to use, as a core material, a crystallized glass that exhibits a large strength (Japanese Unexamined Patent Publication (Kokai) No. 36316/1998, and a fully ceramic artificial crown has been much expected.

In preparing a fully ceramic artificial crown, in general, it is accepted practice to bake various porcelains onto the ceramic core, the porcelains having different color tones for each of the portions of the crown corresponding to constituent portions of a natural tooth in order to realize appearance close to a natural tooth. Concretely speaking with reference to FIG. 1 which is a sectional view of a fully ceramic artificial crown mounted on an abutment tooth P, it is a practice to bake, in the form of layers, a body porcelain A for reproducing an ivory color, an incisal porcelain B for reproducing an incisal color, a translucent porcelain C for producing a transparent feeling and, as required, a cervical porcelain D for reproducing a color of a neck of a tooth on the ceramic core E. These porcelains are generally obtained by blending a powdery ceramic component having an average particle diameter of from about 15 to about 100 µm with pigments that meet use of the porcelains.

A simple baking of the porcelains in an overlapped manner is not enough for reproducing a delicate color tone of a natural tooth or a pattern specific to an individual person. Therefore, it has been done to impart a color by using a porcelains called staining powder that contains a pigment in a relatively large amount, to smooth the surface and to impart transparency by glazing by baking a porcelain called glazing powder which does not almost contain pigment. Here, in order to realize a delicate color and a feeling of high surface quality, the ceramic component in the staining powder or in the glazing powder, usually, has an average particle diameter of from about 1 to about 15 µm, which is smaller than the average particle diameter of the body porcelain and so forth on described above.

And even in these staining powders, glazing powders and the above-mentioned various porcelains porcelains as for the fully ceramic crown having coefficients of linear thermal expansion close to that of the crystallized glass used as the core material, and further having low firing temperatures and improved chemical resistances have been proposed. (Japanese Unexamined Patent Publication (Kokai) No. 139959/2000).

As the methods of producing a ceramic core used for the preparation of a fully ceramic artificial crown, there have been known a casting method in which the crystallization of the crystallized glass is performed by heat treatment after casting a molten crystallized glass into a mold, and a heated/pressurized molding method in which a crystallized glass is softened to a suitable degree without being melted and is poured into a mold to prepare a molded article.

According to the above heated/pressurized molding method, the crystallization of the crystallized glass is happened during the molding, making it possible to shorten the entire working time of molding inclusive of crystallization compared to the casting method, which is an advantage. According to this method, further, the ceramic material is slowly pored into the mold in a highly viscous state of about $10^2$ to $10^6$ poises without heating it nearly to its melting point, hence one can avoid involving bubbles and the reaction such as baking with the investment material (mold material) forming the mold during the molding, and one can obtain a ceramic artificial crown having stable properties (Japanese Unexamined Patent. Publication (Kokai) No. 206782/1999).

Thus, the heated/pressurized molding method exhibits excellent characteristics as a method of producing ceramic cores requiring, however, an extended periods of time for molding the core since the highly viscous material is slowly poured.

In order to shorten the molding time, there can be contrived to increase the rate of molding the crystallized glass by increasing the load at the time of exerting pressure and elevating the temperature at the time of molding.

When the load is increased by using a weight, however, the weight of a large size must be used for the pressurized molding device. Even in other pressurized devices, it is necessary to employ a structure that withstands the pressure, arousing a problem in that the device tends to become bulky. Due to a large load, further, the surface of the investment material is rubbed by the crystallized glass that is poured. Depending upon the investment material that is used, therefore, the surface of the molded article is coarsened or the mold is broken. When the temperature is raised during the pressurized molding, further, the crystallization proceeds faster, and it becomes difficult to control the crystallization and the quality of the obtained core decreases.

According to the heated/pressurized molding method as described above, a new problem arises when it is attempted to shorten the molding time by increasing the load at the time of exerting pressurize or by elevating the molding temperature. It has, therefore, been urged to provide a method of shortening the molding time without accompanied by the above-mentioned problem.

The dental porcelain favorably used as the ceramic core surely exhibits excellent properties. When it is really used, however, the color of the core ceramics tends to be seen through due probably to that light is not suitably scattered inside thereof. To obtain a color tone comparable to that of a natural tooth, therefore, it is necessary for the dental porcelain to impart a suitable degree of transparency which inhibits the underlying color from being seen through.

DISCLOSURE OF THE INVENTION

It is an object of the present invention to develop a method of efficiently producing a fully ceramic artificial crown of a high quality within short periods of time.

In order to overcome the above-mentioned technical assignment, the present inventors have forwarded a keen study. As a result, the inventors have discovered the fact that when a core is molded by using a mold on which surface is formed a film of a solid lubricant by a particular method, the heated crystallized glass can be poured into the mold at an increased rate causing neither the surface coarsening nor the breakage of the mold, and have thus arrived at the present invention.

That is, a first invention is concerned with a method of preparing a ceramic artificial crown by applying at least one kind of dental porcelain selected from the group consisting of a body porcelain, an incisal porcelain and a translucent porcelain onto the surface of a ceramic core molded by heating and softening a ceramic material and putting it into a mold with the application of a pressure followed by firing; wherein said mold is the one formed by burning a wax pattern after having removed a crucible former from an assembly which comprises:

said crucible former having a pole member formed on the central portion of a cylinder with bottom, said pole member having a recessed fitting portion at a central portion in the upper surface thereof;

said wax pattern secured to said recessed fitting portion and applied with a solid lubricant on the surface thereof;

a ring with a backing layer that engages with said cylinder with bottom; and a investment material filled and cured between said ring and a tooth-shaped model; and wherein a portion corresponding to the pole member of the crucible former of said mold is filled with a ceramic material which is, then, pushed by a plunger to mold a ceramic core.

According to the above-mentioned preparation method of the present invention, the wax pattern can be easily secured during the process of making the mold and, besides, the mold is not broken, the surface of the molded article is not coarsened and the crystallization does not lose uniformity even when the flow rate of the ceramic material such as the crystallized glass is increased at the time of molding the ceramic core, making it possible to produce an article of a quality comparable to that of the ceramic cores obtained by the conventional heated/pressurized molding method maintaining good reproduceability. The above effect is obtained probably because when the mold is produced by a particular method as described above, an appropriate lubricating film which lowers the resistance effectively at the time when the ceramic material is inserted is formed on the surface of the mold that comes into contact with the ceramic material.

In the above-mentioned preparation method, it is possible to obtain a highly aesthetic fully ceramic artificial crown by including a step of coloring the surface by applying a surface-coloring material onto the surface of a fired article on which porcelain materials are baked followed by firing, and a step of lustering by applying a glazing powder onto the surface of the fired article obtained through the above step followed by firing. Here, the step of coloring the surface and the step of lustering are favorably effected by applying a kneaded product onto the surface of the fired article obtained in the step preceding said steps followed by firing, said ground product being obtained by grinding a staining powder or a glazing powder each comprising, as a chief sintering component, a glass material containing, on the basis of the oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ with a kneading solution containing not less than 5% by weight of an ester compound having a boiling point of from 100 to 250° C.

In the above preparation method, the solid lubricant is applied to the wax pattern by applying a suspension containing, for example, 0.1 to 30% by weight of a solid lubricant, 0.1 to 20% by weight of an organic binder and the remainder of an organic solvent, followed by drying.

When a crystallizable MgO—CaO—$SiO_2$ glass material is used as a ceramic material, softened so as to possess a viscosity of from $10^2$ to $10^9$ poises and is put into a mold, there takes place the crystallization of the glass material during the molding of the ceramic core, making it possible to efficiently obtain a highly strong ceramic core.

In forming the mold, further, when there is used the crucible former having a pole member of which the diameter is widened downward being tapered at 0.005 to 0.120, it becomes easy to remove the crucible former from the assembly and, besides, the ceramic material being filled in the portion corresponding to the pole member of the former of the mold is not adversely affected even when it is being pushed by a plunger.

When the plunger is made of a ceramic material having a melting point or a decomposition temperature, whichever is lower, which is higher than a temperature of forming the ceramic artificial crown and having a thermal conductivity of not smaller than 0.1 ($cal\cdot cm^{-1}\cdot sec^{-1}\cdot°\ C.^{-1}$) or a coefficient of linear expansion of not larger than $4.0\times 10^{-6}$ (° $C.^{-1}$), there is no need of preheating the plunger at the time of molding the ceramic core, and the molding time can be shortened. When a solid lubricant such as boron nitride or the like is adhered on the surface of the plunger that comes into contact with the ceramic material, further, the plunger can be used again easily after the molding.

The present inventors have further discovered the fact that when a porcelain to which is added an inorganic crystalline powder having a particular refractive index is used, aesthetic property is improved compared to when a conventional porcelain is used.

That is, a second invention is concerned with a dental porcelain used as a body porcelain, an incisal porcelain or a translucent porcelain in the preparation of a ceramic artificial crown, and comprising:

100 parts by weight of a glass material containing, on the basis of the oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$; and 0.1 to 10 parts by weight of an inorganic crystalline powder having a refractive index which is different from the refractive index of the glass material by 0.01 to 0.1, and having an average particle diameter of from 0.1 to 10 μm.

When the above dental porcelain is baked, the color of the underlying ceramic core is blurred maintaining a suitable degree of transparent feeling, and a color tone close to that of a natural tooth can be realized.

Inclusive of the use of the dental porcelain of the present invention, the preparation method of the present invention can be preferably carried out by using a dedicated kit which constitutes the third and fourth inventions.

That is, the third invention is concerned with a kit used for the preparation of a ceramic artificial crown, which comprises:

a crucible former having a pole member formed on the central portion of a cylinder with bottom, said pole member having a recessed fitting portion at a central portion in the upper surface thereof to which a wax pattern is to be secured;

a ring that engages with the cylinder with bottom of said crucible former;

a backing member fitted to the inner surface of the ring;

a investment material filled between the crucible former and the ring;

a plunger for pushing the ceramic member filled in a portion corresponding to the pole member of the crucible former of the mold that is formed by curing the investment material, removing the crucible former and burning the wax pattern; and a container for suspension to apply a solid lubricant onto the wax pattern or onto a portion of the plunger that comes into contact with the ceramics.

The fourth invention is concerned with a kit used for the preparation of a ceramic artificial crown while imparting color and luster, comprising:

a staining powder and a glazing powder each containing, as a sintering component and on the basis of the oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$; and a container for a kneading solution that contains not less than 5% by weight of an ester compound having a boiling point of from 100 to 250° C.

BEST MODE FOR CARRYING OUT THE INVENTION

Figure 1:
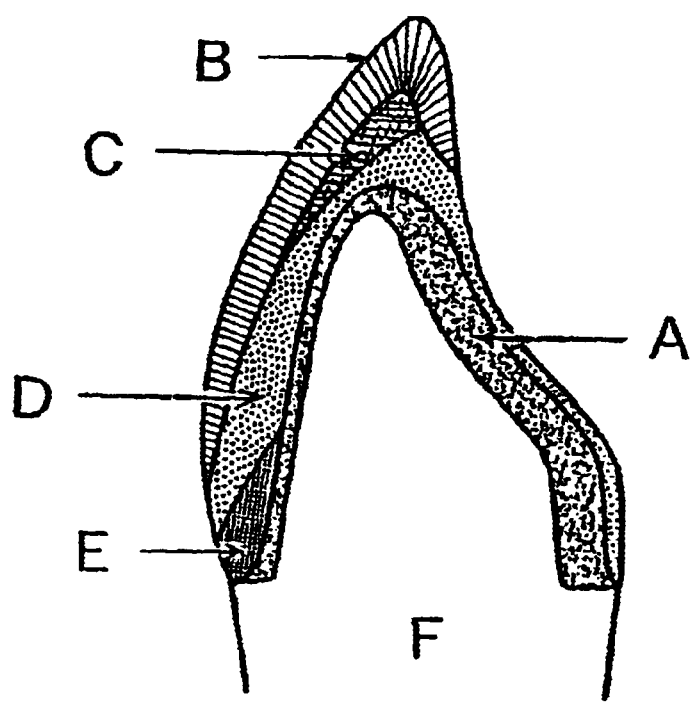
FIG. 1 is a sectional view of a representative fully ceramic artificial crown.

A ceramic material used in the present invention as a starting material of the ceramic core is a nonmetallic inorganic material obtained through the step of heat treatment, and may be any material without particular limitation provided it can be softened and shaped by the application of heat and pressure. A known ceramic material that is generally used as the material for an artificial crown can be used.

Examples of the ceramic material include a glass, a crystallized glass (glass ceramic), bio-ceramic and composite compounds thereof. Among these ceramic materials, it is desired to use a ceramic material which exhibits fluidity in a heated and pressurized state and which will have been crystallized already before being heated at the time of molding or which can be crystallized by heating at the time of molding, since the crown prepared therefrom exhibits excellent abrasion resistance and aesthetic property.

As the ceramic material that will have been crystallized already before being heated at the time of molding, there has been known a material obtained by precipitating leucite crystals having a large coefficient of thermal expansion as a strength-imparting factor in the glass matrix.

As the glass material that can be crystallized by heating at the time of molding, there can be exemplified a glass material in which fine separation of phase takes place due to the heating and the volume crystallization proceeds to turn into a crystallized glass (glass ceramics) and a glass material which contains fine crystals called immature nuclei having a particle diameter of from about 8 to about 30 nm that form crystalline nuclei, the immature nuclei growing through the subsequent heat treatment to turn into a crystallized glass (glass ceramic).

The glass material that contains the crystalline nuclei and turns into the crystallized glass is obtained by treating a $MgO$—$CaO$—$SiO_2$ glass, a $CaO$—$SiO_2$ glass or an $Li_2O$—$SiO_2$ glass at a temperature range near the glass transition temperature or higher by about 100° C. than the glass transition temperature for a predetermined period of time (called nucleus-forming treatment). When the above-mentioned viscosity is maintained, these glass materials permit the volume, crystallization to suitably proceed and turn into crystallized glasses (glass ceramics) suited for preparing a artificial crown.

Among such glass materials, it is particularly preferred to use the $MgO$—$CaO$—$SiO_2$ glass material obtained by melting a starting powder of a composition containing 12 to 26% by weight of MgO, 7 to 16% by weight of CaO, 6 to 19% by weight of $Al_2O_3$, 40 to 50% by weight of $SiO_2$ and 10 to 14% by weight of $TiO_2$ (this glass material belongs to the diopside glass ceramic) disclosed in Japanese Unexamined Patent Publication (Kokai) No. 36316/1998 which is subjected to the nucleus-forming treatment.

In the present invention, the ceramic core is produced by molding in which the ceramic material mentioned above is softend appropriately without melting and put into the mold made by the following specific method.

That is, according to the present invention, a ceramic core is formed by using a mold that is formed by burning a wax pattern after having removed a crucible former from an assembly which comprises said crucible former having a pole member formed on the central portion of a cylinder with bottom, said pole member having a recessed fitting portion at a central portion in the upper surface thereof, said wax pattern fitted into said recessed fitting portion and applied with a solid lubricant on the surface thereof, a ring with a backing layer that engages with said cylinder with bottom, and a investment material filled and cured between said ring and a tooth-shaped model; and filling a portion corresponding to the pole member of the crucible former of the mold with a ceramic material which is, then, pushed by a plunger.

The preparation method of the present invention uses the mold formed by the above-mentioned method. So that, even when the pressure exerted at the time of molding the ceramic core is comparable to that of the conventional heated/pressurized molding method, the ceramic material is put into the mold at an increased rate, and the time for molding the ceramic core can be greatly shortened.

The mold used in the present invention and the method of fabricating the mold will now be described in detail with reference to the drawings.

Figure 2:
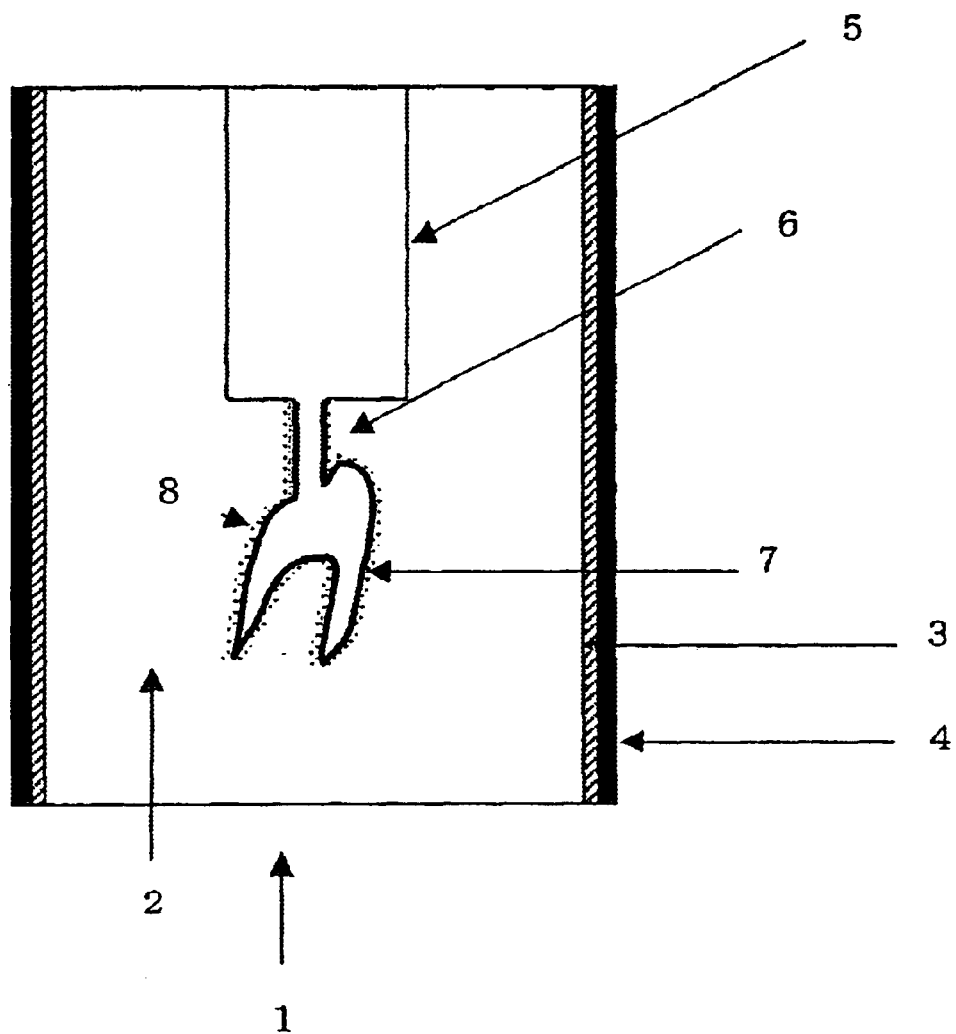
FIG. 2 is a view schematically illustrating in cross section a typical mold used in the present invention.

FIG. 2 is a sectional view of a typical mold used in the present invention. The mold is basically constituted by an investment material 2, a backing member 3 and a ring 4 for casting, and forms therein a cavity constituted by a ceramic material-holding portion 5, a sprue portion 6 and a tooth-shaped portion 7. Here, the ceramic material-holding portion 5 is the one for holding the ceramic material that is a starting material of the core before it is pressurized and also serves as a cylinder when the pressure is to be given by using a plunger. The sprue portion 6 is the one that serves as a sprue runner when the softened ceramic material is put into the tooth-shaped portion 7. The tooth-shaped portion is the one which imparts the final shape of the ceramic core when the ceramic material is put therein and is molded. The ring 4 is for holding the investment material 2 and is made of a cast iron or a stainless steel, and the backing member 3 works to compensate for the expansion of the investment material at the time of heating and is a cloth-like ceramic material.

In the mold 1, a solid lubricant film 8 is formed on the surface of the sprue portion 6 and on the surface of the investment material of the tooth-shaped portion 7. The solid lubricant film 8 may be formed on at least the surface of the investment material of the tooth-shaped portion 7 and needs not necessarily be formed on the surface of the investment material of the sprue portion 6. For obtaining an enhanced effect, however, it is desired that the solid lubricant film is formed on the surface of the investment material of the sprue portion, too.

Next, the method of fabricating the mold 1 will be described with reference to FIG. 3. First, a wax pattern 9 having the shape of the crown core is formed on a gypsum model of a tooth on which a ceramic crown which is an object article will be mounted (the shape of the wax pattern 9 corresponds to the shape of the tooth-shaped portion 7). Next, a sprue line 10 (usually made of wax, and the shape of the sprue line 10 corresponds to the shape of a sprue portion 6) is stuck on the wax pattern 9 and is installed on a pole member 11 (the shape of the pole member corresponds to the shape of the ceramic material-holding portion 5) of the crucible former 11. The crucible former 11 is the one in which the pole member 112 having a recessed fitting portion 113 at the central portion in the upper surface thereof, is formed at the central portion of a cylinder 111 with bottom. The sprue line 10 connected to the wax pattern 9 is fitted to the recessed fitting portion 113, so that the wax pattern 9 is secured. From the standpoint of easy handling and easy moldability, it is desired that the crucible former 11 is the one in which the pole member 112 is tapered at 0.005 to 0.120 to possess a diameter that expands downward and, particularly, the one made of a synthetic rubber for easy removal as proposed already by the present inventors in Japanese Patent Application No. 73916/1999. Here, if two given points of the pole member 112 have heights denoted by h1 and h2 (heights from the upper surface of the bottom of the crucible former 11) and diameters at that heights are denoted by a1 and a2, then, the taper stands for a value defined by the following formula, $$|(a1-a2)/(h1-h2))|.$$

After the wax pattern 9 is secured as described above, a solid lubricant is applied onto the surface of the wax pattern 9 and, as required, onto the surface of the sprue line 10. Then, the solid lubricant is transferred onto the surface of the investment material when the wax pattern is burned and, whereby, a solid lubricant film is formed in the mold, making it possible to shorten the molding time when the ceramic material is put into the mold.

There is no particular limitation on the method of applying the solid lubricant. Preferably, however, a suspension containing a solid lubricant powder, an organic solvent and an organic binder (hereinafter also simply referred to as coating solution) is applied to the surface of the wax pattern 9 and, as required, to the surface of the sprue line 10, and is dried.

There is no particular limitation on the solid lubricant which is a component of the coating solution provided it is a solid that exhibits a lubricating action. Concrete examples of the solid lubricant that can be preferably used in the present invention include tungsten disulfide, carbon fluoride, graphite, β-tantalum sulfide, α-tantalum selenide and boron nitride. These solid lubricants may be used in a single kind or those of different kinds may be used being mixed together. Among the above solid lubricants, it is particularly desired to use the boron nitride because of its very excellent stability at high temperatures.

Though there is no particular limitation, it is desired that the solid lubricant has a particle diameter of from 0.01 to 100 μm from the standpoint of obtaining a high lubricating effect. When the particle diameter is not larger than 0.01 μm, the function of the lubricant decreases. When the particle diameter is not smaller than 100 μm, it becomes difficult to apply the lubricant.

The organic binder used for the coating solution so works that the solid lubricant film containing the organic binder formed on the wax pattern will not be peeled when it is invested in the investment material or is rubbed due to any other technical operation. There is no particular limitation on the organic binder used in the present invention provided it has the above-mentioned function and can be burned when the wax pattern is burned. Concrete examples of the organic binder that can be preferably used include water-soluble organic binders such as polyvinyl pyrrolidone, polyacrylic acid and polyethylene glycol; acrylic resins such as polymethyl methacrylate, polyethyl methacrylate, polyisobutyl methacrylate, and polynormalbutyl methacrylate; vinyl resins such as polyvinylacetic acid; cellulose polymers such as nitrocellulose, ethyl cellulose, cellulose acetate butylate; and water-insoluble organic materials such as alkyd resin, phenol resin, polyester, polystyrene, polycxyethylenecetyl ether, propylene glycol monostearate, digryceryl monostearate, polyoxyethylenestearyl ether, tetraglyceryl tristearate, polyoxyethyleneglycerine monostearate and polyethylenegrycerine monostearate. These organic binders may be used in a single kind or those of different kinds may be used being mixed together.

Among these organic binders, it is desired to use a water-insoluble organic binder because of its particularly high antipeeling effect when invested and, particularly, to use an organic binder which is a water-insoluble polymer having a molecular weight of not smaller than 2000.

The organic solvent in the coating solution contributes to dispersing the solid lubricant, improving applicability and adjusting the thickness of the film. There is no particular limitation on the organic solvent provided it is compatible with the pattern member such as wax and is capable of dissolving the organic binder that is used.

Examples of the organic solvent that can be preferably used include alcohols such as methanol, ethanol, 1-propanol, 2-propanol, 1-butanol, 2-butanol, 2-methyl-1-propanol, 2-methyl-2-propanol, 1-pentanol, 2-pentanol, 3-pentanol, 2-methyl-1-butanol, isopentyl aralcohol, 2-methyl-2-butanol, 3-methyl-2-butanol, 2,2-dimethyl-1-propanol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 3,5,5-trimethyl-1-hexanol, allyl alcohol, propargyl alcohol, cyclohexanol, 1-methylcyclohexanol, 2-methylcyclohexanol, 3-methylcyclohexanol, 4-methylcyclohexanol, abietinol, 1,2-ethanediol, 1,2-propanediol, 1,2-butanediol, 2,3-butanediol, 2-methyl-2,4-pentanediol and 1,2,6-hexanetriol; ether compounds such as diethyl ether, dipropyl ether, diisopropyl ether, dibutylether, dihexyl ether, ethylvinyl ether, butylvinyl ether, dioxane, trioxane, furan, tetrahydrofuran, 1,2-dimethoxyethane, 1,2-diethoxyethane, 1,2-dibutoxyethane, diethylene glycol dimethyl ether, diethylene glycol diethyl ether, diethylene glycol dibutyl ether and acetal; ketone compounds such as acetone, methyl ethyl ketone, methyl propyl ketone, diethyl ketone, butyl methyl ketone, methyl isobutyl ketone, methyl pentyl ketone, dipropyl ketone, duisobutyl ketone, acetonyl acetone, mesityl oxide, phorone, isophorone, methylcyclohexanone and acetophenone; esterified compounds such as methyl formate, ethyl formate, propyl formate, butyl formate, isobutyl foxmate, pentyl formate, methyl acetate, ethyl acetate, propyl acetate, isopropyl acetate, butyl acetate, isobutyl acetate, pentyl acetate, isopentyl acetate, sec-hexyl acetate, 2-ethylbutyl acetato, 2-ethylhexyl acetato, cyclohexyl acetate, benzyl acetate, methyl propionate, ethyl propionate, butyl propionate, isopentyl propionate, methyl butyrate, ethyl butyrate, butyl butyrate, ethylene glycol monoacetato, ethylene diacetate, monoacetin, diacetin, triacetin and diethyl carbonate; hydrocarbon compounds such as pentane, 2-methylbutane, hexane, 2-methylpentane, 2,2-dimethylbutane, 2,3-dimethylbutane, heptane, octane, 2,2,3-trimethylpentane, isooctane, benzene, toluene, xylene, ethylbenzene, methylcyclopentane, cyclohexane, methylcyclohexane, ethylcyclohexane and cyclohexene; and halogenated hydrocarbons such as dichloromethane, chloroform, carbon tetrachloride, 1,1-dichloroethane, 1,2-dichloroethane, 1,1,1-trichloroethane, 1,1,2-trichloroethane, 1,2-dichloroethylene, trichloroethylene, tetrachloroethylene, 1,2-dichloropropane, butyl chloride and 1-chloropentane. These organic solvents may be used in a single kind or those of different kinds maybe used being mixed together.

Among the above-mentioned organic solvents, when there is used the one having a boiling point of from 30 to 200° C., the drying time can be ahortened. It is therefore desired to use the organic solvent having such a boiling point.

The organic solvent used for the coating solution may be suitably selected depending upon the kind of the organic binder that is used. Described below are suitable combinations of the organic binders and the organic solvents.

That is, when an ethyl cellulose is used as the organic binder, the. organic solvent that is used will be chloroform, 1,4-dioxane, 2-propanol, methyl ethyl ketone, 1,2-dimethoxyethane or ethyl acetate. When a polymethyl methacrylate is used as the organic binder, the organic solvent will be xylene, methylene chloride, chloroform, benzene, methyl ethyl ketone, 1,2-dimethoxyethane or ethyl acetate. When a polystyrene is used as the organic binder, the organic solvent will be benzene, ethyl benzene, acetone, tetrahydrofuran, methyl ethyl ketone or ethyl acetate. When a polyvinyl acetate is used as the organic binder, the organic solvent will be benzene, chloroform, methyl ethyl ketone, 1,2-dimethoxyethane or ethyl acetate.

There is no particular limitation on the contents of the solid lubricant, organic binder and organic solvent in the coating solution. From the standpoint of lubricating effect and applicability, however, it is desired that the amount of the solid lubricant is from 0.1 to 30% by weight, the amount of the organic binder is from 0.1 to 20% by weight and the remainder is the organic solvent on the basis of the total weight of the above three.

Further, the combination is not limited the one of a single kind of organic solvent and a single kind of organic binder, but may be those of plural kinds of organic solvents and plural kinds of organic binders. For example, when the ethyl cellulose and the polymethyl methacrylate are used as the organic binder, there may be used such solvents as methyl ethyl ketone, 1,2-dimethoxyethane, ethyl acetate and heptane in combination.

To the coating solution may be added various additives such as surfactant and the like that are contained in a solution applied before the technical operation within a range of not impairing the effect of the present invention.

There is no particular limitation on the method of preparing the coating solution or on the method of applying the coating solution onto the wax pattern 9 (and, as required, onto the sprue line 10). For example, the coating solution obtained by mixing the components of predetermined amounts in a container made of a plastic, a glass or a metal, is applied to the surface of the wax pattern by spraying or by using a brush. Or, the wax pattern is dipped in the coating solution (immersed and taken out).

In this case, it is desired that the coated film has a thickness of from 5 to 100 $\mu$m after drying. The coated film having a thickness lying in this range is not peeled off when it is invested, and not only improves the rate of introducing the ceramic material into the mold but also improves the quality of the obtained molded article.

In order to improve compatibility to the coating solution, it is desired to apply a surfactant in advance onto the surface of the wax pattern on where the coating solution will be applied prior to applying the coating solution. As the surfactant, there can be used a known surfactant of the ionic type or the nonionic type without any limitation. The solid lubricant may be applied to the wax pattern before it is secured to the crucible former. From the standpoint of operability, however, it is desired to apply the solid lubricant after the wax pattern is secured.

Figure 3:
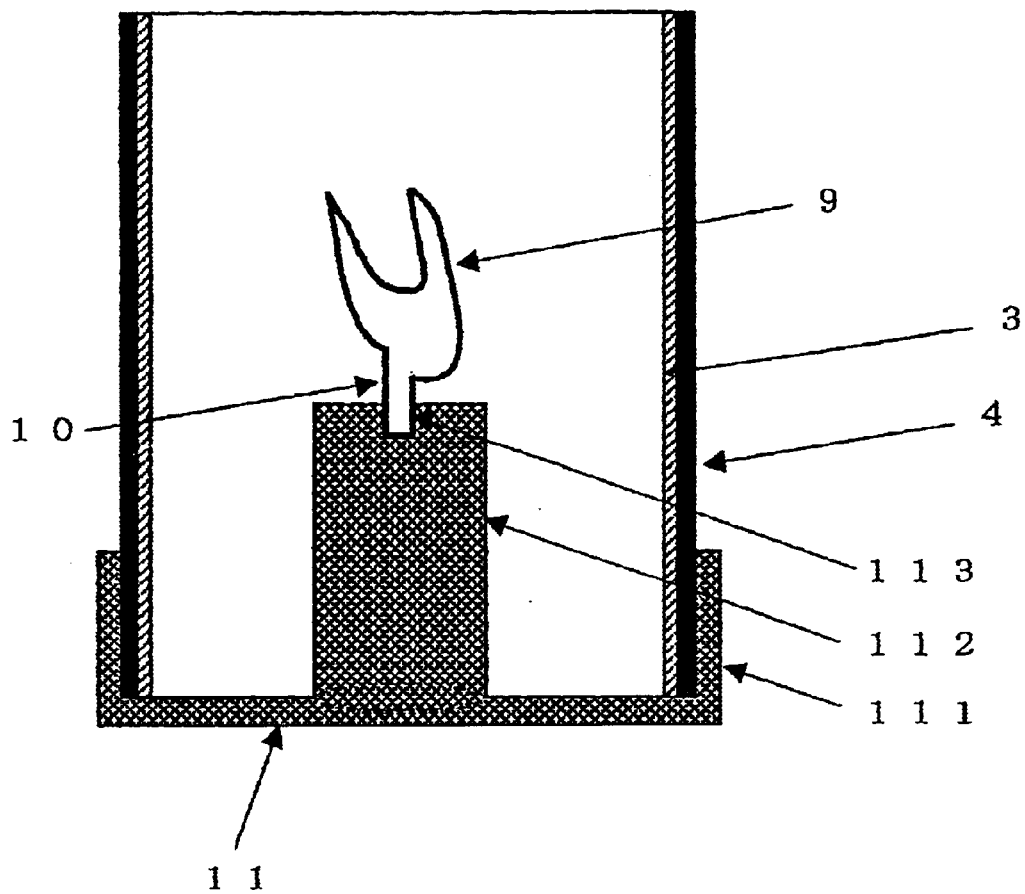
FIG. 3 is a view schematically illustrating in cross section of when a casting ring and a backing member is set to a crucible former to which is secured a wax pattern in preparing a mold used in the present invention.

Then, the backing member 3 and the casting ring 4 are set to the crucible former 11 in which the wax pattern 9 and the like are set as shown in FIG. 3, and the investment material is poured on the inside of the casting ring 4 and the backing member 3 so that the wax pattern 9, sprue-line 10 and pole member of the crucible former 11 are invested therein. Thereafter, the investment material is cured. After the investment material has been cured, the crucible former 11 is removed, and the investment material is heated to burn the wax pattern 9 and the sprue line 10 therein, thereby to prepare the mold 1.

The materials used in the method of fabricating the mold 1 are those that are used in an ordinary casting method or heated/pressurized molding method except the coating solution. For example, the investment material is the one of the phosphate type, cristobalite type or gypsum that is generally used. Among them, it is particularly desired to use the investment material of gypsum since it permits the molded article to be easily taken out and makes it possible to obtain a molded article having a surface luster. As for the wax for wax pattern, sprue line and backing member, there can be used those which have been placed in the market as the materials for dental use without any limitation.

By using the thus obtained mold, a ceramic core is molded in the same manner as by the conventional heated/pressurized molding method. Namely, the ceramic material-holding portion (corresponding to the pole member of the crucible former) of the mold is filled with the ceramic material which is the starting material. The ceramic material is, then, heated and softened, and is pushed by a plunger so as to be molded.

Here, it is desired that the ceramic material which is the starting material has been molded in advance in the shape of a pole member so as to be loosely inserted in the ceramic material-holding member 5 maintaining a clearance of 0.3 to 0.8 mm and having a volume slightly larger (by 10 to 50%) than the total volume of the sprue portion 6 and the tooth-shaped portion 7 of the mold. When the crystallized glass is used as the ceramic material, it is desired to effect the above-mentioned pre-molding to also form the nuclei mentioned earlier.

There is no particular limitation on the heating temperature at the time of pushing the ceramic material provided it is lower than the melting point of the ceramic material. From the standpoint of molding, however, it is desired that the temperature is such that the ceramic material assumes a viscosity of from $10^2$ to $10^9$ poises or the temperature is lower than the melting point by 100 to 500° C. For example, when the above-mentioned crystallized glass is used as the ceramic material, the heating temperature is usually from 800° C. to 1200° C. The melting point of the ceramic material can be defined to be a temperature at which the ceramic material assumes a viscosity of $10^2$ poises.

The thus heated and softened ceramic member is introduced into the mold by being pressurized by the plunger, and is molded into a ceramic core. As the plunger used here, it is prefer to use the plunger which is made of a ceramic material having a melting point or a decomposition temperature, whichever is lower, which is higher than a temperature of molding the ceramic crown, and having a thermal conductivity of not smaller than 0.1 (cal·cm$^{-1}$·sec$^{-1}$·° C.$^{-1}$) or having a coefficient of linear expansion of not larger than $4.0 \times 10^6$ (° C.$^{-1}$) because it is not broken by a heat shock that results from a sudden heating to omit the preheating and, hence, to shorten the molding time.

Further, from the standpoint of easily removing the ceramic material adhered to the plunger after the ceramic core has been molded and of lengthening the life of the plunger that is repetitively used, it is desired to apply the solid lubricant such as boron nitride to a portion of the plunger that comes in contact with the ceramic material in the like manner when it is applied to the wax pattern at the time of preparing the mold.

There is no particular limitation on the pressurizing method or on the pressurizing condition at the time of molding, and the load may be exerted by placing a weight, by transmitting the force of a motor to the piston through gears or by pressurizing the piston using the compressed air to produce a pressure of from about 2 to about 20 kg/cm$^2$. In order that the crystallization takes place uniformly at the time of molding to obtain a ceramic core of a high quality, it is desired to execute the two-step pressurization; i.e., the sprue portion 6 is filled with the ceramic material under 300 to 500 g/cm$^2$ and the tooth-shaped portion 7 is filled with the ceramic material under a pressure which is greater by more than 10 times thereof as disclosed in Japanese Unexamined Patent Publication (Kokai) No. 206782/1999. The two-step pressurization can be favorably conducted by using an electric furnace capable of executing the pressing with the compressed air, such as EP-500 (manufactured by IVOCLAR Co.) or by using an electric furnace for heated/pressurized molding method employing a particular weight loading system as disclosed in Japanese Unexamined Patent Publication (Kokai) No. 226976/1999. The ceramic member introduced into the mold is removed from the mold by breaking the mold after cooled like in the conventional heated/pressurized molding method and is, then, polished as required to obtain a ceramic core.

As will be obvious from the foregoing description, the ceramic core according to the preparation method of the present invention is molded by using a dedicated kit that comprises (i) a crucible former having a pole member formed on the central portion of a cylinder with bottom, said pole member having a recessed fitting portion at a central portion in the upper surface thereof with which a wax pattern is to be fitted, (ii) a ring that engages with the cylinder with bottom of said crucible former, (iii) a backing member fitted to the inner surface of the ring, (iv) a investment filled between the crucible former and the ring, (v) a plunger for pushing the ceramic member filled in a portion corresponding to the pole member of the crucible former of the mold that is formed by curing the investment, removing the crucible former and burning the wax pattern, and (vi) a container for containing a suspension for applying a solid lubricant onto the wax pattern or onto a portion of the plunger that comes into by, contact with the ceramics.

According to the preparation method of the present invention, various porcelains such as body porcelain, incisal porcelain and translucent porcelain are baked on the surface of the thus obtained ceramic core and, as required further, the coloring and lustering treatment is effected by baking a staining powder and a glazing powder.

Here, the body porcelain, the incisal porcelain or the translucent porcelain is desirably a dental porcelain (second invention) which is a composition comprising:

100 parts by weight of a glass material containing, on the basis of oxides, 57 to 65% by weight of $SiO_2$, 8 to 18% by weight of $Al_2O_3$, 15 to 25% by weight of $B_{2O3}$, 0.1 to 2% by weight of ZnO, 3 to 7% by weight of $Na_2O$ and 2 to 8% by weight of $Li_2O$, and, particularly, having a coefficient of linear expansion of not larger than $6 \times 10^{-6}$ (1/° C.); and 0.1 to 10 parts by weight of an inorganic crystalline powder having a refractive index which is different from the refractive index of the glass material by 0.01 to 0.1, and having an average particle diameter of from 0.1 to 10 μm, from the standpoint of firing, at a temperature lower than the distortion point of the core, the dental porcelain on the core of the glass ceramic of diopside that has a coefficient of linear expansion of as low as 4 to $6 \times 10^{-6}$ (1/° C.), permitting little generation of stress that stems from a difference in the contraction at the time of firing and cooling, obtaining a high chemical resistance such as resistance against being dissolved in an acidic solution, and obtaining a suitable degree of transparency for blurring the color of the underlying core.

Here, the glass material used for the dental porcelain of the present invention may be the same as the glass material that is used for the dental porcelain disclosed in Japanese Unexamined Patent Publication (Kokai) No. 139959/2000. As also described in the above publication, the porcelain containing the glass material as a chief component can be fired on the core of the diopside glass ceramic at a temperature lower than the distortion point of the core, little generates stress that stems from a difference in the contraction at the time of firing and cooling, and exhibits a high chemical resistance such as resistance against being dissolved in an acidic solution. From the standpoint of obtaining these features to a conspicuous degree, it is desired that the glass material contains, on the basis of the oxides, 57 to 62% by weight of $SiO_2$, 10 to 15% by weight of $Al_2O_3$, 15 to 20% by weight of $B_2O_3$, 1 to 2% by weight of ZnO, 3 to 7% by weight of $Na_2O$ and 3 to 8% by weight of $Li_2O$, and, particularly, has a coefficient of linear expansion of not larger than $6 \times 10^{-6}$ (1/° C.).

In the present invention, there is added, per 100 parts by weight of the glassnmaterial, 0.1 to 10 parts by weight of an inorganic crystalline powder having a refractive index which is different from the refractive index of the glass material by 0.01 to 0.1, and having an average particle diameter of from 0.1 to 10 μm, in order to suitably lower the degree of transparency after baking so that the color of the underlying core will not appear conspicuously, thereby to obtain a color tone close to that of a natural tooth. The above-mentioned effect is not obtained when the inorganic powder added to the glass material is not crystalline but is amorphous, or when the inorganic powder to be added to the glass material has at least any one of the refractive index, particle diameter or amount of addition that lies outside the above-mentioned ranges though it is crystalline. From the standpoint of the effect, it is more desired that the difference (Δ) in the diffractive index is from 0.04 to 15 0.1, the particle diameter is from 0.1 to 5 μm and the amount of addition (parts by weight per 100 parts by weight of the glass material) is from 0.1 to 10 parts by weight.

There is no particular limitation on the inorganic crystalline powder used for the dental pottery material of the present invention provided its refractive index is different from the refractive index of the glass material by from 0.01 to 0.1. Here, the refractive index stands for that of the powder at 23° C., and can be measured by a method (liquid immersion method) in which a refractive index of a liquid organic medium having a predetermined refractive index is regarded to be the refractive index when the liquid becomes transparent by immersing the powder in the liquid. The refractive index of the above liquid organic medium can be measured by using the Abbe, refractometer. In general, the glass material has a refractive index of from 1.45 to 1.55. Therefore, preferred examples of the inorganic crystalline powder will be a quartz (refractive index of 1.54) which is a crystal of silicon dioxide, a cristobalite (refractive index of 1.48), tridymite (refractive index of 1.48), leucite (refractive index of 1.51), eucryptite (refractive index of 1.58), nepheline (refractive index of 1.53) and a cordierite (refractive index of 1.54).

In the dental porcelain of the present invention, the particle size of the glass material is adjusted depending upon the use, the inorganic crystalline powder is mixed and, then, a pigment and an oxidizing agent are added thereto.

Concretely speaking, in the case of the body porcelain or the incisal porcelain,the particle diameter of the glass material is so adjusted as to possess an average particle diameter of from 15 to 100 μm, and the pigment is blended in an amount of from 0.01 to 3 parts by weight per 100 parts by weight of the glass material.

In the case of the translucent porcelain, it is desired that the-particle diameter of the glass material is so adjusted as to possess an average particle diameter of from 5 to 100 μm, and a white pigment is blended in an amount of smaller than 3 parts by weight per 100 parts by weight of the glass material.

The above pigment is added to impart a color to the porcelain after baking and to control the transparency. Here, however, since the porcelain is fired at a high temperature, the pigment that is used is usually an inorganic pigment. Representative examples of the inorganic pigment that can be preferably used include vanadium yellow, cobalt blue, chrome pink, iron chrome brown, titanium white and zirconia white.

The oxidizing agent which, as required, is added to the dental porcelain of the present invention is the one that is added so that an organic material contained as an impurity is incorporated in the porcelain without completely decomposed during the firing and, hence, to prevent deterioration in the color tone of the porcelain. There is no particular limitation on the oxidizing agent provided it serves as a source of supplying oxygen. Among them, there is preferably used a sulfate which exhibits a mild oxidizing action and which by itself sublimates at a temperature lower than the firing temperature and does not remain in the fired article and, particularly, an ammonium sulfate $\{(NH_4)_2SO_4\}$. Though there is no particular limitation on the amount of addition, the oxidizing agent is usually added in an amount of from about 0.1 to 5 parts by weight per 100 parts by weight of the glass.

The dental porcelain of the present invention is baked on the ceramic core by applying the porcelains onto the ceramic core followed by firing. There is no particular limitation on the method of application and on the firing method, and there can be employed known methods that are usually used for the porcelains without limitation. For example, the powder of the porcelain is kneaded with water, applied onto the ceramics that becomes the core, and is fired. It is desired that various porcelains are applied in plural layers as shown in FIG. 1. It is desired that the firing temperature is from 680 to 740° C. for all of the body porcelain, incisal porcelain and translucent porcelain.

In the preparation method of the present invention, the ceramic core onto which various porcelains are baked may be used as the artificial crown. To obtain a more aesthetic artificial crown, however, it is desired to effect a step of coloring the surface by applying a surface-coloring material onto the surface of a fired article on which a porcelain is baked followed by firing, and a step of lustering by applying a glazing powder onto the surface of the fired article obtained through the above step followed by firing.

Here, the coloring agent (staining powder) is desirably a glass material containing, on the basis of the oxides, 57 to 65% by weight of $Sio_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ and, particularly, having a coefficient of linear expansion of not larger than $6 \times 10^{-6}$ (1/° C.) that is disclosed in Japanese Unexamined Patent Publication (Kokai) No. 139959/2000 while adjusting the particle diameter so as to possess an average particle diameter of from 1 to 15 μm and being blended with 1 to 15 parts by weight of a pigment per 100 parts by weight of the glass material.

When used as the glazing powder, further, the particle diameter of the glass material disclosed in Japanese Unexamined Patent Publication (Kokai) No. 139959/2000 is so adjusted as to possess an average particle diameter of from 1 to 15 μm, and this glass material is used without blended with any additive.

The staining powder and the glazing powder are usually applied by being kneaded with a kneading solution. Here, it is desired to use a kneading solution having a refractive index close to that of the porcelain since the kneaded mud thereof is translucent making it easy to predict the color tone after firing. In particular, it is desired to use a kneading solution for the dental porcelain containing not less than 5% by weight of an ester compound having a boiling point of from 100 to 250° C. and, especially, a kneading solution for the dental porcelain containing from 10 to 90% by weight of an ester compound having a boiling point of from 100 to 250° C. and 90 to 10% by weight of a polyhydric alcohol having 3 to 8 carbon atoms, since it does not permit the organic material to remain after firing, does not cause the color to be blackened, exhibits favorable compatibility with the powder, and does not permit the powder to be dried during the kneading.

Examples of the ester compound having a boiling point of 100 to 250° C. include propyl acetate, isopropyl acetate, butyl acetate, isobutyl acetate, sec-butyl acetate, pentyl acetate, isopentyl acetate, 3-methoxybutyl acetato, sec-hexyl acetate, 2-ethylbutyl acetate, 2-ethylhexyl acetato, cyclohexyl acetate, benzyl acetate, isobutyl isobutyrate, ethyl 2-hydroxy-2-methylpropionate, butyl propionate, isopentyl propionate, butyl butyrate, isopentyl butyrate, ethyl isovalerate, isopentyl isovalerate, methyl benzoate, ethyl benzoate, propyl benzoate, butyl benzoate, isopentyl benzoate, ethyl cinnamate, γ-butyrolactone, β-butyrolactone, diethyl oxalate, dibutyl oxalate, dipentyl oxalate, diethyl malonate, dimethyl maleate, diethyl maleate, dibutyl maleate, tributyl citrate, ethylene glycol monoacetate, ethylene diacetate, ethylene glycol monoformic acid ester, ethylene glycol monobutyric acid ester, ethylene glycol monooleic acid ester, ethylene glycol diformic acid ester, ethylene glycol dipropionic acid ester, ethylene glycol monoacetato, monoacetin, diacetin, triacetin and propylene carbonate.

Among these ester compounds, it is desired to use cyclic ester compounds because of their less odor and favorable dripping property, and it is particularly desired to use a γ-butyrolactone (boiling point of 204° C.) or a β-butyrolactone (boiling point of 172° C.).

As the polyalcohol having 3 to 8 carbon atoms, further, there can be used propylene glycol, 1,2-butanediol, 1,3-butanediol, 2,3-butanediol, dipropylene glycol, 2-methylpentanediol, and 2-ethyl-1,3-hexanediol.

It is desired that the staining powder and the glazing powder are baked at 650 to 710° C.

As will be obvious from the foregoing description, the step of coloring and the step of lustering can be favorably executed by using a kit which comprises:

(i) a stained powder and a glazing powder each containing, as a sintering component and on the basis of the oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$; and (ii) a container for a kneading solution that contains not less than 5% by weight of an ester compound having a boiling point of from 100 to 250° C.

EXAMPLES

The significance of when the preparation method of the present invention is compared with the conventional preparation method resides in that the preparation method of the present invention makes it possible to shorten the molding time without deteriorating the quality of the ceramic core and permits the color of the underlayer to be less transmitted when the dental porcelain is baked. Concerning these points, therefore, Examples of the invention will be described in comparison with Comparative Examples. It should, however, be noted that the invention is in no way limited to these Examples only.

I. Moldability of the Ceramic Core

The ceramic material (also referred to as starting ceramic material) that is the starting material of the ceramic core and the mold used in Examples and in Comparative Examples were prepared as described below.

(1) Preparation of the Starting Ceramic Material.

92.08 Grams of $SiO_2$, 28.16 g of MgO, 36.85 g of $CaCO_3$, 31.04 g of $Al(OH)_3$, and 22.63 g of $TiO_2$ were pulverized by using a ball mill and were mixed together as starting materials. The mixture was introduced into a platinum crucible and was heated and melted at 1500° C. for one hour in an electric furnace. Then, the molten glass was poured into the mold and was gradually cooled so as to be pre-molded into a pole member having a volume larger by about 20% than the total volume of the sprue portion 6 and the tooth-shaped portion 7 of the mold so as to be loosely inserted in the ceramic material-holding portion 5 maintaining a clearance of about 0.5 mm. The thus pre-molded glass member was put into the electric furnace, and was heat-treated at 700° C. for 5 hours so that fine crystals were precipitated in the glass. Here, the temperature was raised at a rate of 300° C./h and, then, the glass material was left to cool in the furnace down to room temperature to thereby form nuclei. The glass material in which the nuclei were formed (also called starting glass ingot) was used for the heated/pressurized molding.

The obtained starting glass ingot exhibited a viscosity at 900° C. of $10^6$ poises. After maintained in this state for 20 minutes and cooled, the starting glass ingot was identified for its precipitated crystals by the X-ray diffraction method. The diopside crystals had been precipitated from which it was confirmed that upon heating, the glass material was crystallized. The melting point of the glass material was 1300° C.

(2) Preparation of the Mold.

A sprue line of a line wax {trade name: Ready Casting Wax, manufactured by GC Co.} of a diameter of 3.2 mm and a length of 7 mm was attached to a wax pattern {trade name: Natural Wax Pattern C, manufactured by Nisshin Co.} of a premolar of the lower jaw, and was secured to the crucible former.

Then, a predetermined coating solution was applied onto the surface of the wax pattern secured to the crucible former, and was dried. Thereafter, a casting ring {trade name: JM casting ring, manufactured by Fujiwara Shika Sangyo Co.} and a crystal ribbon {trade name: GC New Casting Liner, manufactured by GC Co.] was, set to the crucible former. The coating solution was applied such that the thickness of the coated film after drying was 20 μm. The applied coating solution was dried by being left to stand in the open air.

Then, a investment material mud {trade name; OK Powder, manufactured by GC Co.} was poured into the inner side of the casting ring and the crystal ribbon (backing member) so that the wax pattern secured to the crucible former was invested therein. After the investment material was cured, the crucible former was removed, followed by heating at 800° C. to burn the wax pattern and the sprue line at 800° C. thereby to prepare the mold.

Example 1

A coating solution was prepared from 4 parts by weight of a boron nitride powder having an average particle diameter of 2 μm, 2 parts by weight of an ethyl cellulose and 94 parts by weight of a methyl ethyl ketone. By using the mold prepared by using the above coating solution, the heated/pressurized molding was conducted in a manner as described below.

That is, the mold was, first, put into a ring furnace {trade name: VR7, manufactured by KDF Co.}, heated up to 800° C. at a rate of 50° C. a minute over about 15 minutes, and was maintained at this temperature for 45 minutes to pre-heat the mold. After pre-heated, the cylindrical plunger and the starting glass ingot were fitted to the ceramic-holding portion of the mold, which was then introduced into a heated/pressurized furnace that has been heated in advance at 900° C. Thereafter, the starting glass ingot was maintained at 900° C. which was a pressing temperature for 10 minutes, and the glass material softened to a sufficient degree was pressurized at this temperature with apressing load of 7.2 kg/cm² via a plunger so as to be put into the mold. After completely put into the mold, the glass material was maintained at 900° C. for another 10 minutes and was, then, cooled. The mold was then broken and the molded article was taken out; i.e., the ceramic core was prepared.

The heated/pressurized furnace used the electric furnace {trade name: FM-X, manufactured by Yamato Kagaku Co.} in which the pressurizing device of the weight load type was incorporated, and a moment when the glass material was completely poured into the mold was determined by,monitoring the distance of motion of the piston by using a digital gauge {trade name: IDA-112M, manufactured by Mitutoyo Co.}.

The molding time was 16 minutes, and the surfaces of the molded article had not been coarsened.

Comparative Example 1

A molded article was prepared by the heated/pressured molding method in the same manner as in Example 1 but using the mold that was prepared without using the coating solution. The molding time was 25 minutes, and the surfaces of the molded article had not been coarsened.

A comparison of Example 1 with Comparative Example 1 tells that the molding time in Example 1 was shortened by about 30% compared to that of Comparative Example 1 under the same pressure.

Examples 2 to 25

The molds were prepared in the same manner as in Example 1 but replacing the coating solution used for the preparation of the mold by the coating solutions of the compositions shown in Table 1, followed by the heatedipressurized molding in the same manner as in Example 1, and the press-moldability (molding time) and the surface states of the molded articles were evaluated. The results were as shown in Table 2.

The molding times and the surface states of the molded articles were evaluated by using the molds prepared without applying the coating solution to the wax pattern and with the pressure of 7.2 kg/cm² (Comparative Example 1) as a reference. The molding times were evaluated to be "○" when they have been shortened by more than 30%, to be "Δ" when the times were shortened by more than 15%, to be "▽" when the times were shortened not by more than 15%, and to be "−" when there was no difference from Comparative Example 1. Further, the surface states were evaluated to be "○" when there was no difference from the molded article of Comparative Example 1, and to be "X" when the surfaces were coarsened or the color tone has changed.

Table 1 also shows the composition of the coating solution used in Example 1, and Table 2 also shows the evaluated results of Example 1.

TABLE 1

| Ex. No. | Solid lubricant | | Organic binder | | Organic solvent | |
| --- | --- | --- | --- | --- | --- | --- |
| 1 | boron nitride, | 4 pts by wt | ethyl cellulose, | 2 pts by wt | methyl ethyl ketone, | 94 pts by wt |
| 2 | boron nitride, | 2 pts by wt | cellulose acetate butyrate, | 8 pts by wt | acetone, | 90 pts by wt |
| 3 | boron nitride, | 10 pts by wt | polyvinyl acetate, | 10 pts by wt | methyl ethyl ketone, | 80 pts by wt |
| 4 | boron nitride, | 4 pts by wt | polymethyl methacrylate, | 4 pts by wt | ethanol, | 92 pts by wt |
| 5 | boron nitride, | 0.1 pt by wt | polybutyl methacrylate, | 2 pts by wt | butyl methyl ketone, | 97.9 pts by wt |
| 6 | boron nitride, | 30 pts by wt | polystyrene, | 1 pt by wt | 2-propanol, | 69 pts by wt |
| 7 | boron nitride, | 4 pts by wt | polyvinyl pyrrolidone, | 8 pts by wt | dipropyl ether, | 88 pts by wt |
| 8 | boron nitride, | 20 pts by wt | polyacrylic acid, | 10 pts by wt | methyl ethyl ketone, | 70 pts by wt |
| 9 | boron nitride, | 10 pts by wt | polyethylene glycol, | 20 pts by wt | isopropyl ketone, | 70 pts by wt |
| 10 | boron nitride, | 8 pts by wt | hydroxypropyl cellulose, | 5 pts by wt | acetone, | 87 pts by wt |
| 11 | boron nitride, | 15 pts by wt | ethyl cellulose, | 2 pts by wt | 1,2-dimethoxyethane, | 83 pts by wt |
| 12 | boron nitride, | 4 pts by wt | polystyrene, | 4 pts by wt | ethyl acetate, | 92 pts by wt |
| 13 | boron nitride, | 30 pts by wt | polymethyl methacrylate, | 6 pts by wt | 2-propanol, | 64 pts by wt |
| 14 | boron nitride, | 5 pts by wt | ethyl cellulose, | 6 pts by wt | acetone, | 89 pts by wt |
| 15 | boron nitride, | 20 pts by wt | cellulose acetate butyrate, | 8 pts by wt | propyl acetate, | 72 pts by wt |
| 16 | boron nitride, | 10 pts by wt | ethyl cellulose, | 10 pts by wt | butyl methyl ketone, | 80 pts by wt |
| 17 | boron nitride, | 3 pts by wt | polymethyl methacrylate, | 0.1 pt by wt | ethyl acetate, | 96.9 pts by wt |
| 18 | boron nitride, | 2 pts by wt | polystyrene, | 5 pts by wt | toluene, | 93 pts by wt |
| 19 | boron nitride, | 8 pts by wt | ethyl cellulose, | 10 pts by wt | ethanol, | 82 pts by wt |
| 20 | boron nitride, | 20 pts by wt | ethyl cellulose, polymethyl methacrylate, | 2 pts by wt, 1 pt by wt | 1,2-dimethoxyethane, | 77 pts by wt |
| 21 | boron nitride, | 4 pts by wt | cellulose acetate butyrate,, polymethyl methacrylate, | 1 pt by wt, 4 pts by wt | 1,2-dimethoxyethane, | 91 pts by wt |
| 22 | boron nitride, | 10 pts by wt | ethyl cellulose, polyvinyl acetate, | 1 pts by wt 2 pts by wt | ethyl acetate, | 87 pts by wt |
| 23 | boron nitride, | 15 pts by wt | ethyl cellulose, polystyrene, | 1 pt by wt, 2 pts by wt | acetone, | 82 pts by wt |
| 24 | boron nitride, | 20 pts by wt | ethyl cellulose, | 2 pts by wt | methyl ethyl ketone, 1,2-dimethoxyethane, | 47 pts by wt 31 pts by wt |
| 25 | boron nitride, | 5 pts by wt | ethyl cellulose, polymethyl methacrylate, | 1 pt by wt. 1 pt by wt | methyl ethyl ketone, 1,2-dimethoxyethane, | 47 pts by wt 46 pts by wt |

TABLE 2

| Ex. No. | Press load/ kgcm⁻² | Press temp./ ° C. | Press-moldability | Surface coarseness |
| --- | --- | --- | --- | --- |
| 1 | 7.2 | 900 | ○ | ○ |
| 2 | 7.2 | 900 | ○ | ○ |
| 3 | 7.2 | 900 | ○ | ○ |
| 4 | 7.2 | 900 | ○ | ○ |
| 5 | 7.2 | 900 | ○ | ○ |
| 6 | 7.2 | 900 | ○ | ○ |

TABLE 2-continued

| Ex. No. | Press load/ kgcm$^{-2}$ | Press temp./ °C. | Press-moldability | Surface coarseness |
|---|---|---|---|---|
| 7 | 7.2 | 900 | △ | ○ |
| 8 | 7.2 | 900 | △ | ○ |
| 9 | 7.2 | 900 | △ | ○ |
| 10 | 7.2 | 900 | △ | ○ |
| 11 | 7.2 | 900 | ○ | ○ |
| 12 | 7.2 | 900 | ○ | ○ |
| 13 | 7.2 | 900 | ○ | ○ |
| 14 | 7.2 | 900 | ○ | |
| 15 | 7.2 | 900 | ○ | ○ |
| 16 | 7.2 | 900 | ○ | ○ |
| 17 | 7.2 | 900 | ○ | ○ |
| 18 | 7.2 | 900 | ○ | ○ |
| 19 | 7.2 | 900 | ○ | ○ |
| 20 | 7.2 | 900 | ○ | ○ |
| 21 | 7.2 | 900 | ○ | ○ |
| 22 | 7.2 | 900 | ○ | ○ |
| 23 | 7.2 | 900 | ○ | ○ |

TABLE 2-continued

| Ex. No. | Press load/ kgcm$^{-2}$ | Press temp./ °C. | Press-moldability | Surface coarseness |
|---|---|---|---|---|
| 24 | 7.2 | 900 | ○ | ○ |
| 25 | 7.2 | 900 | ○ | ○ |

Comparative Example 2

The heated/pressurized molding was conducted in the same manner as in Comparative Example 1 but setting the pressure (also referred to as pressing load) during the pressing to be 10 kg/cm². As a result, the molding time was shortened by 30%, but the surface state of the molded article was worsened.

Comparative Example 3

The heated/pressurized molding was conducted in the same manner as in Comparative Example 1 but setting the heating temperature during the molding to be 920° C. As a result, the molding time was shortened by 30%. However, the crystallization proceeded so much that the molded article was whitened.

When the heated/pressurized molding was conducted by go using the mold prepared without using the coating solution as in Comparative Examples 2 and 3, the molding time could be shortened by increasing the pressing load or by elevating the temperature at which the heated/pressurized molding was effected causing, however, the surface of the molded article to be coarsened and the color tone to be changed.

Comparative Example 4 and Examples 26 to 28

The molds were prepared in the same manner as in Example 1 but replacing the coating solution used for the preparation of the mold by the coating solutions of the compositions shown in Table 3, followed by the heated/pressurized molding in the same manner as in Example 1, and the press-moldability (molding time) and the surface states of the molded articles were evaluated. The results were as shown in Table 3.

Table 3 also shows the results of Comparative Examples 1 to 3.

TABLE 3

| Comp. Ex. No. | Solid Lubricant | Organic binder | Organic solvent | Press load/ kgcm$^{-2}$ | Press temp./ °C. | Press mold-ability | Surface coarseness |
|---|---|---|---|---|---|---|---|
| 1 | none | none | none | 7.2 | 900 | — | ○ |
| 2 | none | none | none | 10 | 900 | ○ | X |
| 3 | none | none | none | 7.2 | 920 | ○ | X |
| 4 | none | ethyl cellulose 2 pts by wt | methyl ethyl ketone 98 pts by wt | 7.2 | 900 | — | ○ |
| Ex. No. 26 | boron nitride 4 pts by wt | none | methyl ethyl ketone, 96 pts by wt | 7.2 | 900 | ▽ | ○ |
| Ex. No. 27 | boron nitride 35 pts by wt | ethyl cellulose 65 pts by wt | none | 7.2 | 900 | ▽ | ○ |
| Ex. No. 28 | boron nitride 4 pts by wt | none | none | 7.2 | 900 | ▽ | ○ |

A comparison of Example 1 with Comparative Example 4 tells that when there is used no solid lubricant, the pressing rate is not enhanced.

From Examples 1, 26 and 17, when an organic binder is used, the solid lubricant film is not peeled, contributing to improving the pressing rate.

In Examples 27 and 28, further, the drying required an extended period of time since there was used no organic solvent.

II. Properties of the Porcelains

The porcelains were evaluated concerning their optimum firing temperatures, coefficients of thermal expansion, solubilities, color differences and transparencies. These properties were measured by the methods described below.
(1) Determining the Optimum Firing Temperatures.

A sample porcelain and water were kneaded together and were introduced while being condensed into a mold having a thickness of 2 mm and a hole of a diameter of 10 mm to prepare a molded article. Seven molded articles were prepared for each of the glass compositions, and were fired at temperatures each differed by 10° C. over a range of 30° C. above and 30° C. below the firing temperature which was expected from each composition and of which the last digit being rounded off.

The firing was conducted under the conditions of using a Porcelain Furnace Sigma 120 (manufactured by Tokuyama Co.) which is an automatic electric furnace having a function capable of setting a temperature-raising pattern in advance, introducing the crucible in which the molded article has been contained into the furnace after having dried it in advance in a furnace heated at 500° C. for 5 minutes, raising the temperature at a rate of 25°/min and maintaining a desired firing temperature for 2 minutes.

The fired articles were observed, and the firing temperatures were regarded to be optimum firing temperatures when there were obtained the fired articles which have been entirely and completely sintered to become translucent, the surfaces thereof without being completely melted but exhibiting a slight degree of ruggedness due to pottery material particles.

(2) Evaluation of Coefficient of Thermal Expansion.

A rectangular parallelopiped measuring 2 mm×2 mm×10 mm was cut out from the sintered article of the above sample pottery material to use it as a sample for measurement, and was heated from room temperature up to 500° C. by using a thermoanalyzer TMA 120 (manufactured by Seiko Denshi Co.) to measure the coefficient of thermal expansion.

(3) Evaluation of Amount Dissolved in an Acid.

The amount dissolved in an acid was found by calculating the loss of mass $\mu g/cm^2$ of a test piece of the sintered article of the sample porcelain in accordance with the Soxhlet extraction method with 4% acetic acid conducted for 16 hours as stipulated under the International Standards (ISO 6872). The test piece was prepared by using a mold having a diameter of 16 mm and a thickness of 1.6 mm.

(4) Evaluation of Color Difference and Transparency.

A sample porcelain and water were kneaded together and were introduced while being condensed into a mold having a thickness of 1.6 mm and a hole of a diameter of 16 mm to prepare a molded article. Then, the molded article was put into a crucible and was fired at a temperature best suited for the porcelain sample by using an automatic electric furnace (Porcelain Furnace Sigma 120, manufactured by Tokuyama Co.) having a function capable of setting a temperature-raising pattern in advance.

After firing, the molded article was cooled and was taken out, and was machined by using a rotary grinder into a thickness of 1 mm to prepare a sample for measurement.

By using a spectrocolorimeter TC-1800MK-II (manufactured by Tokyo Denshoku Co.), the thus prepared sample for measurement was measured for its $L^*_W$, $a^*_W$ and $b^*_W$ in the case when the background color was white and $L^*_B$, $a^*_B$ and $b^*_B$ in the case when the background color was black, and a color difference $\Delta E^*$ due to the background color was calculated in compliance with the following formula.

Further, the transparency was calculated in compliance with the following formula depending upon the Y-value of when the background color was white and the background color was black. Here, the Y-value stands for the one among X-value, Y-value and Z-value which are the three stimulating values.

Color difference $(\Delta E^*) = ((L^*_W - L^*_B)^2 + (a^*_W - a^*_B)^2 + (b^*_W - b^*_B)^2)^{1/2}$ Transparency $(C) = 1 - (Y$-value of when the background color is black$/Y$-value of when the background color is white$)$ The smaller the value $\Delta E^*$, the smaller the appearance of color (the smaller the degree of underlying color that is seen through). Further, the larger the C-value, the higher the transparency.

Example 29

30.4 Grams of silicon dioxide (special grade chemical, manufactured by Wako Junyaku Co.), 8.3 g of aluminum hydroxide (special grade chemical, manufactured by Kanto Kagaku Co.), 8.7 g of boron oxide (special grade chemical, manufactured by Wako Junyaku Co.), 4.7 g of lithium carbonate (special grade chemical, manufactured by Wako Junyaku Co.), 4.0 g of sodium carbonate (special grade chemical, manufactured by Wako Junyaku Co.) and 1.1 g of zinc oxide (special grade chemical, manufactured by Wako Junyaku Co.) were weighed and mixed, and the mixture was melted at 1300° C. for 2 hours and was flown onto a stainless steel plate and was cooled to obtain a uniform glass in the same manner as in Example 1 of Japanese unexamined Patent Publication (Kokai) No. 139959/2000. Analysis of the thus obtained glass composition indicated 61% by weight of $SiO_2$, 11% by weight of $Al_2O_3$, 18% by weight of $B_2O_3$, 4% by weight of $Li2O$, 5% by weight of $Na_2O$ and 2% by weight of $ZnO$ on the basis of the oxides. Further, the refractive index of the glass was measured by the solution immersion method to be 1.504.

Next, the obtained glass was pulverized into a powder having an average particle diameter of 37 $\mu$m in an agate mortar. To 100 parts by weight of the thus obtained glass powder was added 3 parts by weight of quartz (silicon dioxide crystals having a refractive index of 1.544) of an average particle diameter of 1.5 $\mu$m, and the two components were mixed well to obtain a sample porcelain.

The sample porcelain was measured for its optimum firing temperature, coefficient of thermal expansion, amount of dissolution in an acid, color difference and transparency. The results were as shown in Table 4.

Further, the above sample porcelain and water were kneaded, applied onto the ceramic core prepared in Example 1 and was fired at a firing temperature of 700° C. As a result, a favorable baking was accomplished without cracking on the surface of the porcelain and without peeling between the porcelain and the core. There was not observed, either, deformation of the ceramic core due to the baking of the porcelain.

Comparative Example 5

Properties were measured in the same manner as in Example 29 but using a glass powder without containing quartz powder as a sample pottery material. The results were as shown in Table 4.

TABLE 4

| | Optimum firing temp (° C.) | Coefficient of therm expansion (× $10^{-6}$ ° C.) | Amount of dissltn in acid ($\mu$G/cm2) | Color difference | Transparency |
|---|---|---|---|---|---|
| Ex. No. 29 | 710 | 5.5 | 21 | 8.65 | 0.15 |
| Comp. Ex. No. 5 | 700 | 5.5 | 19 | 12.54 | 0.23 |

In Example 29 as shown in Table 4, the transparency is slightly deteriorated compared to that of Comparative Example 5 in which no quartz powder is mixed, and the color difference $\Delta E^*$ decreases suppressing the appearance of color.

When baked onto the ceramic core in the same manner as in Example 29, favorable results were obtained as in Example 29.

According to the method of preparing a ceramic artificial crown of the present invention, the molding time can be shortened without decreasing the quality of the obtained ceramic core. In the heated/pressurized molding method, further, weld lines often develop at a portion where the flows meet in the molded articles. The method of the invention, however, effectively prevents the occurrence of weld lines.

When the dental porcelain of the invention is used in the step of baking the porcelain, further, there is obtained a fully ceramic artificial crown exhibiting excellently aesthetic appearance close to that of a natural tooth without affected by the color of the underlying ceramic core.

What is claimed is:

1. A method of preparing a ceramic artificial crown comprising steps of:

molding a ceramic material heated and softened to a ceramic core by putting the ceramiic material into a mold with the application of a pressure;

applying at least one kind of dental porcelain selected from a the group consisting of a body porcelain, an incisal porcelain and a translucent porcelain onto the surface of the ceramic core; and firing the dental porcelain; and wherein, said mold for moldg the ceramic material is formed by burning a wax pattern after having removed a crucible former from an assembly which comprises:

said crucible former having a pole member formed on the central portion of a cylinder with bottom, said pole member having a recessed fitting portion at a central portion in the upper surface thereof;

said wax pattern secured to said recessed fitting portion and applied with a solid lubricant on the surface thereof;

a ring with a backing layer that engages with said cylinder with bottom; and an investment material filled and cured between said ring and, a tooth-shaped model; and wherein the ceramic core is molded by filing the ceramic material to a portion, which corresponds to the pole member, in the mold and then pushing the ceramic material by a plunger.

2. A method of preparing a ceramic artificial crown according to claim 1, further comprising the following steps;

coloring a surface of a fired article on which the dental porcelain is baked, by applying a surface-coloring material onto said surface and by firing, lustering a colored surface obtained through the above step by applying a glazing powder onto the colored surface and by firing.

3. The method according to claim 2 further comprising applying the solid lubricant to the wax pattern by applying a suspension comprising the solid lubricant, an organic binder and an organic solvent, followed by drying.

4. The method according to claim 3 wherein said suspension comprises from 0.1 to 30% by weight of the solid lubricant, from 0.1 to 20% by weight of the organic binder and the remainder of the organic solvent.

5. The preparation method according to claim 4 wherein the ceramic material put into the mold has a viscosity of from $10^2$ to $10^9$ poises.

6. The preparation method according to claim 5 wherein the ceramic material is a crystalline MgO—CaO—SiO$_2$ glass material.

7. The preparation method according to claim 6 further comprising providing the pole member of the crucible former with a diameter which widens downward and is tapered at 0.005 to 0.120.

8. The preparation method according to claim 7 further comprising providing said plunger made of a ceramic material having a melting point or decomposition temperature, whichever is lower, which is higher than a temperature of forming the ceramic artificial crown and having a thermal conductivity of not smaller than 0.1 (cal·cm$^{-1}$·sec$^{-1}$·° C.$^{-1}$) or a coefficient of linear expansion of not larger than $4.0 \times 10^{-6}$(° C.$^{-1}$).

9. The preparation method according to claim 8 further comprising adhering a solid lubricant in advance onto the surface of the plunger that comes into contact with the ceramic material.

10. The preparation method according to claim 9 further comprising applying a dental porcelain onto the surface of the ceramic core, followed by baking, wherein the dental porcelain applied is a kneaded product obtained by kneading with water a body porcelain, an incisal porcelain or a translucent porcelain which comprises:

100 parts by weight of a glass material containing, on the basis of the oxides, 57 to 65% by weight of SiO$_2$, 8 to 18% by weight of Al$_2$O$_3$, 15 to 25% by weight of B$_2$O$_3$, 0.1 to 2% by weight of ZnO, 3 to 7% by weight of Na$_2$O and 2 to 8% by weight of Li$_2$O; and 0.1 to 10 parts by weight of an inorganic crystalline powder having a refractive index which is different from the refractive index of the glass material by 0.01 to 0.1, and heaving an average particle diameter of farm 0.1 to 10 µm.

11. The preparation method according to claim 10 further comprising coloring and lustering the surface of said crown by applying a kneaded product to the surface of the fired article, followed by firing, wherein the kneaded product is obtained by kneading a staining powder and a glazing powder, each comprising, as a chief sintering component, a glass material containing, on the basis or oxides, 57 to 65% by weight of sir, 8 to 18% by weight of Al$_2$O$_3$, 15 to 25% by weight of B$_2$O$_3$, 0.1 to 2% by weight of ZnO, 3 to 7% by weight of Na$_2$O and 2 to 8% by weight of Li$_2$O with a kneading solution containing not less than 5% by weight of an ester compound having a boiling point of from 100 to 250° C.

12. The method according to claim 1 further comprising applying the solid lubricant to the wax pattern by applying a suspension comprising the solid lubricant, an organic binder and an organic solvent, followed by drying.

13. The method according to claim 12 wherein said suspension comprises from 0.1 to 30% by weight of the solid lubricant, from 0.1 to 20% by weight of the organic binder and the remainder of the organic solvent.

14. The preparation method according to claim 1 wherein the ceramic material put into the mold has a viscosity of from $10^2$ to $10^9$ poises.

15. The preparation method according to claim 14 wherein the ceramic material is a crystalline MgO—CaO—SiO$_2$ glass material.

16. The preparation method according to claim 1 wherein the ceramic material is a crystalline MgO—CaO—SiO$_2$ glass material.

17. The preparation method according to claim 1 further comprising providing the pole member of the crucible former with a diameter which widens downward and is tapered at 0.005 to 0.120.

18. The preparation method according to claim 1 further comprising providing said plunger made of a ceramic material having a melting point or decomposition temperature, whichever is lower, which is higher than a temperature of forming the ceramic artificial crown and having a thermal conductivity of not smaller than 0.1 (cal·cm$^{-1}$·sec$^{-1}$·° C.$^{-1}$) or a coefficient of linear expansion of not larger than $4.0 \times 10^{-6}$ (° C.$^{-1}$).

19. The preparation method according to claim 1 further comprising adhering a solid lubricant in advance onto the surface of the plunger that comes into contact with the ceramic material.

20. The preparation method according to claim 1 further comprising applying a dental porcelain onto the surface of the ceramic core, followed by baking, wherein the dental porcelain applied is a kneaded product obtained by kneading with water a body porcelain, an incisal porcelain or a translucent porcelain which comprises:

100 parts by weight of a glass material containing, on the basis of the oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8t by weight of $Li_2O$; and 0.1 to 10 parts by weight of an inorganic crystalline powder having a refractive index which is different from the refractive index of the glass material by 0.01 to 0.1, and having an average particle diameter of from 0.1 to 10 $\mu$m.

21. The preparation method according to claim 20 further comprising coloring and lustering the surface of said crown by applying a kneaded product to the surface of the fired article, followed by firing, wherein the kneads product is obtained by kneading a staining powder and a glazing powder, each comprising, as a chief sintering component, a glass material containing, on the basis of oxides, 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ with a kneading solution containing not less than 5% by weight of an ester compound having a boiling point of from 100 to 250° C.

22. The preparation method according to claim 1 further comprising coloring and lustering the surface of said crown by applying a kneaded product to the surface of the fired article, followed by firing, wherein the kneaded product is obtained by kneading a staining powder and a glazing powder, each comprising, as a chief sintering component, a glass material containing, on the basis of oxides, 57 to 65% by weight of $SiO_2$, 8 to 18% by weight of $Al_2O_3$, 15 to 25 by weight of $B_2O_3$, 0.1 to 2% by weight of ZnO, 3 to 7% by weight of $Na_2O$ and 2 to 8% by weight of $Li_2O$ with a kneading solution containing not less than 5% by weight of an ester compound having a boiling point of from 100 to 250° C.

* * * * *